United States Patent [19]
Reppert

[11] Patent Number: 6,037,131
[45] Date of Patent: Mar. 14, 2000

[54] MELATONIN 1A RECEPTOR GENE REGULATORY REGIONS AN USES THEREOF

[75] Inventor: Steven M. Reppert, Newton, Mass.

[73] Assignee: The General Hospital Corporation, Boston, Mass.

[21] Appl. No.: 09/280,420

[22] Filed: Mar. 29, 1999

Related U.S. Application Data

[62] Division of application No. 08/895,701, Jul. 17, 1997, Pat. No. 5,889,177.

[51] Int. Cl.[7] ..................................... C12Q 1/68
[52] U.S. Cl. ............................................. 435/6
[58] Field of Search .................................... 435/6

[56] References Cited

U.S. PATENT DOCUMENTS 5,856,124   1/1999   Reppert et al. .................. 435/69.1

FOREIGN PATENT DOCUMENTS

WO 95 35320   12/1995   WIPO.

OTHER PUBLICATIONS

Albarracin, C.T. et al. (1994) "Isolation and Charact4erization of the 5'–Flanking Region of the Mouse Gonadotropin–Releasing Hormone Receptor Gene," *Endocrinology* 135:2300–2306.

Bartess, T.J. and Goldman, B.D. (1989) "Mammalian pineal Melatonin. A clock for all seasons," *Experientia* 45:939–945.

Carlson, L.L. et al. (1989) "Melatonin Signal Transduction in Hamster Brain: Inhibition of Adenylyl Cyclase by a Pertussis Toxin–Sensitive G Protein" *Endocrinology* 125:2670–2676.

Chomczynski, P., and Sachhi, N. (1987) "Single–Step Method of RNA Isolation by Acid Gaundinium Thiocyanate–Phenol–Chlororform Extraction," *Anal. Biochem* 162:159–159.

Cullen, B.R. (1987)"Use of Eukaryotic Expression Technology in the Functional Analysis of cloned Genes," *Methods Enzymol.* 152:684–704.

Dubocovich, M.L. and Takahashi, J.S. (1987) "Use of 2–[$^{125}$I] Iodomelatonin to Characterize Melatonin Binding Sites in Chicken Retina," *Proc. Natl. Acad. Sci. USA* 84:3916–3920.

Hahn, S. et al. (1989) Yeast TATA–binding Protein TFIID Binds to TATA elements with Both Consensus and non–consensus DNA sequences *Proc. Natl. Acad. Sci. USA* 86:5718–5722.

Hammang, J.P. et al. (1990) "Immortalized Retinal Neurons Derived from SV40 T–Antigen–Induced Tumors in Transgenic Mice," *Neuron* 4:775–782.

Heckert, L.L. et al. (1992) "Structural Organization of the Follicle–Stimulating hormone Receptor Gene," *Molecular Endocrinology* 6:70–80.

Ikuyama, S. et al. (1992) "Characterization of the 5'–Flanking Region of the Rat Thyrotropin Receptor Gene," *Molecular Endocrinology* 6:793–804.

Jackson, R.J. and Standart, N. (1990) "do the Poly(A) Tail and 3' Untranslated Region Control mRNA Translation?" *Cell* 62:15–24.

Karsch, F.J. et al. (1984) "Neuroendocrine Basis of Seasonal Reproduction," *Recent Prog. Horm. Res.* 40:185–232.

Laitinen, J.T. and Saavedra, J.M. (1990) "Characterization of Melatonin Receptors in the Rat Suprachiasmatic Nuclei: Modulation of Affinity with Cations and Guanine Nucleotides," *Endocrinology* 126:2110–2115.

Morgan, P.J. et al. (1989) "Guanine Nucleotides Regulate the Affinity of Melatonin Receptors on the Ovine Pars tuberalis," *Neuroendocrinology* 50:359–362.

Morgan, P.J. et al. (1990) "Both Pertussis Toxin–Sensitive and Insensitive G–Proteins Link Melatonin Receptor to Inhibition of Adenylate Cyclase in the Ovine Pars Tuberalis," *J. Neuroendocrinol.* 2:773–776.

Mahle, C.D. et al. (1994) "Desensitization of the Melatonin–Mediated Functional Response in RT2–2 Retinal Neuronal Cells," Abstract, *24th Annual Meeting Soc. Neuroscience,* Miami, FL, p. 535.

Reppert, S.M. et al. (1988) "Putative Melatonin Receptors in a Human Biological Clock," *Science* 242:78–81.

Reppert, S.M. et al. (1991) "Molecular Cloning and Characterization of a Rat A$_1$–Adenosine Receptor that is Widely Expressed in Brain and Spinal Cord," *Mol. Endocrinol.* 5:1037–1048.

Reppert, S.M. et al. (1994) "Cloning of a Structural and Functional Homolog of the Circadian Clock Gene period from the Giant Silkmoth Antheraea pernyi," *Neuron* 13:1167–1176.

Reppert, S.M. et al. (1994) "Cloning and Characterization of a Mammalian Melatonin Receptor That Mediates Reproductive and Circadian Responses," *Neuron* 13:1177–1185.

Reppert, S.M. et al. (1995) "Melatonin Receptors Are for the Birds: Molecular Analysis of Two Receptor Subtypes Differentially Expressed in Chick Brain," *Neuron* 15:1003–1015.

Reppert, S.M. et al. (1996) "Melatonin receptors step into the light: cloning and classification of subtypes," *Trends in Pharmacological Sciences* 17:100–102.

(List continued on next page.)

*Primary Examiner*—James Ketter
*Attorney, Agent, or Firm*—Fish & Richardson P.C.

[57] ABSTRACT

Disclosed are DNAs encoding melatonin 1*a* receptor gene promoter regions, recombinant polypeptides expressed from such DNAs, and methods of using such expression constructs to screen for promoter activators or inhibitors. Transcriptional activators are useful as therapeutics to reentrain endogenous melatonin rhythms as a means of treating circadian rhythm disorders in humans and control reproductive cycles in seasonally breeding animals. Transcriptional inhibitors are useful as therapeutics to control the initiation or timing of puberty in humans.

6 Claims, 5 Drawing Sheets

OTHER PUBLICATIONS

Rivkees, S.A. et al. (1989) "Guanine nucleotide–binding protein regulation of melatonin receptors in lizard brain," *Proc. Natl. Acad. Sci. USA* 86:3882–3886.

Roca, A.L. et al. (1996) "Structure, Characterization, and Expression of the Gene Encoding the Mouse $Mel_{1a}$ Melatonin Receptor," *Endocrinology* 137:3469–3477.

Rosenthal, N. (1987) "Identification of Regulatory Elements of Cloned Genes with Functional Assays," *Methods Enzymol.* 152:704–720.

Rozen, F. et al. (1995) "Structure, characterization, and expression of the rat oxytocin receptor gene," *Proc. Natl. Acad. Sci. USA* 92:200–204.

Sachs, A.B. (1993) "Messenger RNA Degradation in Eukaryotes," *Cell* 74:413–421.

Singer, V.L. et al. (1990) "A wide variety of DNA sequences can functionally replace a yeast TATA element for transcriptional activation," *Genes and Development* 4:636–645.

Slaugenhaupt, S.A. et al. (1995) "Mapping of the Gene for the $Mel_{1a}$–Melatonin Receptor to Human Chromosome 4 (MTNR1A) and Mouse Chromosome 8 (Mtnr1a)," *Genomics* 27:355–357.

Treacy, M.N. et al. (1991) "I–POU: a POU–domain protein that inhibits neuron–specific gene activation," *Nature* 350:577–584.

Tsai–Morris, C.H. et al. (1991) "Structural Organization of the Rat Luteinizing Hormone (LH) Receptor Gene," *J. Biol. Chem.* 266:11355–11359.

Vaněček, J. (1988) "Melatonin Binding Sites," *J. Neurochem.* 51:1436–1440.

Weaver D.R. et al. (1991) "Localization of Melatonin Receptors in Mammalian Brain," *Suprachiasmatic Nucleus: the Mind's Clock.* Klein, D.C., Moore, R.Y, and Reppert, S.M., eds. New York: Oxford Univ. Press; pp. 289–308.

de Wet, J.R. et al. (1987) "Firefly Luciferase Gene: Structure and Expression in Mammalian Cells," *Mol. Cell. Biol.* 7:725–737.

Wobbe, C.R. and Struhl. K. (1990) "Yeast and Human TATA–Binding Proteins Have Nearly Identical DNA Sequence Requirements for Transcription In Vitro," *Mol. Cell. Biol.* 10:3859–3867.

Lyon et al., "Mouse Genome," *Continuation of Mouse Newsletter,* 93(1):23, 38–39, 1995.

Reeck et al., "Homology in proteins and nucleic acids: a terminology muddle and a way out of it", Cell, 50:667.

FIG. 2A

```
TACATTTGCCACAGCCTGAACTACGACAAATATACAGTAACAAGAACTGCTCTACGTGTTCCTGATATGGATGCTGACACTCATC  +583
 Y  I  C  H  S  L  K  Y  D  K  I  Y  S  N  K  N  S  L  C  Y  V  F  L  I  W  M  L  T  L     160
                            └──────┘                  └──────────────────────────┘
                                                                  IV

GCCATCATGCCCAACCTGCAAACCGGAACTGCCAGTACTCCTGTACCTTCACCCAGTCTGTCAGCTAC                      +673
 A  I  M  P  N  L  Q  T  G  T  L  Q  Y  D  P  R  I  Y  S  C  T  F  T  Q  S  V  S  S  A  Y   190

ACGATAGCAGTGGTTGTTTCCATTTGTGCCTATGATTATTCTCTGTGCTACTTAAGGATATGGGTCTCTGGTCCTTCAGTC         +763
 T  L  A  V  V  Y  F  H  F  I  V  P  M  I  I  V  I  E  C  Y  L  R  I  W  Y  L  V  Q  V      220
    └────────────────────────────────────────────────┘
                        V

AGACGGAGGGTGAAACCCGACAACAAGCCCAAACTGAAGCCCCAGGACTTCAGGAACTTTGTCACCATGTTCGTAGTTTTTGTACTTTTT +853
 R  R  R  V  K  P  D  N  K  P  K  L  K  P  Q  D  F  R  N  F  V  T  M  F  V  V  F  V  L  F     250

GCCATTGTTGGGCCCCACTCAACTCATAGTCTTATTGTGCCTAGACACCCTGCCACCATGGTCCCCAGATCCCAGAGTGGCTGTTC    +943
 A  I  C  W  A  P  L  N  L  I  G  L  I  Y  A  S  D  P  A  T  M  V  P  R  I  P  E  W  L  F   280
    └───────────────────────────┘
                 VI

GTGGCTAGTTACTACCTGGCTACTTCAACAGCTGCCTTCAACAGCTGTAATTATATACGGACTGCTCAACCAGAATTCAGAAAGGAATACAAA +1033
 V  A  S  Y  Y  L  A  Y  F  N  S  C  I  N  A  I  Y  G  L  L  N  Q  N  F  R  K  E  Y  K         310
    └──────────────────────────────┘
                  VII

AAGATTATTGTCTCGTTGTGCACAGCCAAGATGTTCTTTGTGGAGAGTTCAAATGAAGAAGCAGATAAGATTAAATGTAAGCCCTCTCCA   +1123
 K  I  I  V  S  L  C  T  A  K  M  F  F  V  E  S  S  N  E  E  A  D  K  I  K  C  K  P  S  P      340

CTAATACCCAATAATAATCTTATTAAAGTGGACTGTCTGTTTAAAAGCCAGTGCTGTCTAGCAGATTATCCACACTGGTTGGGGTCTTCCTG  +1213
 L  I  P  N  N  N  L  I  K  V  D  S  V  -  (SEQ ID NO:2)                                        353

CTCTCCTTGTGTTGCTTTTTCTTTTGTCTAGAAATCAGTCTATCCAACTTGAAGCTCTTCAGGTGCCTCCATAGTGTTGGAAAGGATCTCC  +1303
TGTCTGCCCATAATCAGATTGCTAGTAGTGTCCTCTCTGGGGAATGCTCAAGGGAATGCTAGTATCAAGACACCATAGTTTAAATGACAACTGTATCAGAGAGAG +1393
GTCGTGGTGTGACAGCTCTCGTCTTCGGGCAACCAGTCTGTTGCCACAGTGGTTGCCACACTAGTTTAGGATTACAATATACAGCAACAGCCAAAC          +1483
TGAACAAATGTGGAAGAACTCAAGAGAGGGACCTTCCTTTTATTGTAAGCGAGTGATACAGAGTGTTATTCTTAC                              +1573

CTATGGCTGAATTAAAATAGTCAAAAAACTTAA                                                         +1606
       Poly(A) signal
            <- exon 2  |    (SEQ ID NO:1)
```

FIG. 2B   (contains SEQ ID NOS:1 & 2)

MELATONIN 1A RECEPTOR GENE REGULATORY REGIONS AN USES THEREOF

CROSS REFERENCE TO RELATED APPLICATIONS

This application is a division of Ser. No. 08/895,701, filed Jul. 17, 1997, now U.S. Pat. No. 5,889,177; claims priority from provisional application 60/022,185, filed on Jul. 18, 1996.

STATEMENT AS TO FEDERALLY SPONSORED RESEARCH

This invention was made at least in part with funds from the Federal government (NIH grant R37 HD 14427), and the government therefore has rights in the invention.

BACKGROUND OF THE INVENTION

The invention relates to nucleic acids encoding transcriptional regulatory sequences of a high-affinity melatonin receptor gene.

The high-affinity melatonin receptor is a membrane protein that is coupled to guanine nucleotide binding proteins (G proteins). G proteins, in turn, communicate ligand-activated receptor signals to the appropriate intracellular effector system(s). The hormone, melatonin, inhibits adenylyl cyclase causing a decrease in intracellular cyclic AMP (cAMP) concentration.

Melatonin, the principal hormone of the vertebrate pineal gland, elicits potent neurobiological effects. Melatonin influences circadian rhythm and mediates the effects of photoperiod on reproductive function in seasonally breeding mammals. In humans, melatonin administration has been shown to alleviate the symptoms of jet lag after air travel across several time zones. The hormone also has potent sedative effects in humans and may be a useful hypnotic agent.

Melatonin exerts its photoperiodic and circadian effects through pharmacologically specific, high-affinity receptors (Dubocovich, M. L. and Takahashi, J., *Proc. Natl. Acad Sci. USA* (1987) 84:3916–3920; Vanecek, J., *J. Neurochem.* (1988) 51:1436–1440; Reppert et al., (1988) supra). In seasonally breeding mammals, pineal melatonin secretion regulates seasonal responses to changes in day length (Bartness, T. J. and Goldman, B. D., *Experientia* (1989) 45:939–945; Karsch et al., *Recent Prog. Homm. Res.* (1984) 40:185–232). The only site containing melatonin 1a receptors in all photoperiodic species examined to date (Weaver, et al., *Suprachiasmatic nucleus: the mind's clock.* Klein, D. C., Moore, R. Y, and Reppert, S. M., eds. New York: Oxford University Press; (1991) pp. 289–308) is the pars tuberalis (PT), a portion of the pituitary gland. In contrast to other species, in humans melatonin 1a receptors are not consistently present in the PT.

High-affinity melatonin 1a ($Mel_{1a}$) receptors are located in discrete regions of the vertebrate central nervous system of several mammalian species, including humans. Binding studies using the ligand 2-[$^{125}$I]-iodomelatonin ($^{125}$I-melatonin or [$^{125}$I]MEL) have identified high-affinity melatonin 1a receptors ($K_d < 2 \times 10^{-10}$ M) in sites such as the suprachiasmatic nuclei (SCN), the site of a biological clock that regulates numerous circadian rhythms (Reppert et al., *Science* (1988) 242:78–81). To date, high-affinity melatonin receptors have not been identified in central nervous system tissues other than brain.

Receptor affinity is sensitive to guanine nucleotides and activation of the receptors consistently leads to the inhibition of adenylyl cyclase through a pertussis toxin-sensitive mechanism (Rivkees, S. A. et al., *Proc. Natl. Acad. Sci. USA* (1989) 86:3883–3886; Carlson, L. L. et al., *Endocrinology* (1989) 125:2670–2676; Morgan, P. J. et al., *Neuroendocrinology* (1989) 50:358–362; Morgan, P. J. et al., *J. Neuroendocrinol.* (1990) 2:773–776; Laitinen, J. T. and Saavedra, J. M., *Endocrinology* (1990) 126:2110–2115). High-affinity melatonin receptors thus appear to belong to the superfamily of G protein-coupled receptors.

SUMMARY OF THE INVENTION

In general, the invention features substantially pure DNA (cDNA or genomic DNA) encoding the 3' and 5' transcriptional regulatory regions and coding region of a high-affinity melatonin 1a receptor in brain. In preferred embodiments, the invention includes nucleotide sequences for 5' and 3' transcriptional regulatory regions of a melatonin 1a receptor gene. Such sequences of the invention include a promoter as well as upstream and downstream enhancer elements and/or cis- and trans-acting factor binding sites functional in the transcriptional regulation of the melatonin 1a receptor gene. Sequences functional in the transcription of the melatonin 1a receptor gene may be located more than 1.5 kilobase pairs from the start or termination of the receptor coding sequence. In other preferred embodiments of the invention, the transcriptional regulatory sequences make up a portion of SEQ ID NO:1. The nucleotide sequence of the coding regions and the amino acid sequence of the melatonin 1a receptor is also included in SEQ ID NO:1 and are disclosed in applicant's U.S. application Ser. No. 08/261,857 filed Jun. 17, 1994, Ser. No. 08/319,887 filed Oct. 7, 1994, and Ser. No. 08/446,103 filed Jun. 6, 1995, which applications are incorporated herein by reference in their entirety.

In various preferred embodiments, the transcriptional regulatory regions are derived from a vertebrate animal, such as a mouse, human, or sheep.

In an aspect of the invention, a nucleic acid construct is provided which includes a melatonin 1a promoter operably linked to a gene of interest, such as a reporter gene. Preferably, a melatonin 1a promoter has a nucleotide sequence substantially identical to a portion of SEQ ID NO:1 that contains transcriptional regulatory sequences of a melatonin 1a receptor gene.

In an embodiment of the invention, the melatonin 1a transcriptional regulatory region of the construct hybridizes under stringent hybridization conditions to a nucleic acid molecule having a nucleotide sequence of SEQ ID NO:1.

In another embodiment, the construct of the invention includes a melatonin 1a regulatory region having approximately 95% homology to transcriptional regulatory sequences of SEQ ID NO:1.

In other related aspects, the invention features vectors which contain such isolated DNA and which are preferably capable of directing expression of a gene of interest encoded by the DNA in a vector-containing cell; and cells containing such vectors (preferably eukaryotic cells, e.g., RT2-2 cells (obtained from C. Mahle, Bristol-Myers Squibb, New Jersey) or CHO cells (ATCC; Cat. No. CCL 61 or COS-7 cells (ATCC; Cat. No. CRL 1651). Preferably, such cells are stably transfected with such isolated DNA.

In another aspect, the invention features a method of screening candidate compounds for their ability to alter transcription from a functional melatonin 1a receptor gene promoter. The method involves: a) providing a cell comprising a recombinant mouse melatonin 1a receptor gene promoter operably linked to a reporter gene; b) contacting the cell with a candidate compound; and c) monitoring the expression of the reporter gene in the presence of the candidate compound.

In preferred embodiments, the method includes a cell comprising a recombinant melatonin 1a receptor gene promoter, which promoter has a nucleotide sequence substantially identical to transcriptional regulatory sequences of SEQ ID NO:1.

In another preferred embodiment, the promoter is capable of hybridizing under stringent hybridization conditions to a nucleic acid molecule having a nucleotide sequence complementary to SEQ ID NO:1, and preferably the portion of SEQ ID NO:1 corresponding to part or all of the 5' untranslated region and/or the 3' untranslated region.

In yet another preferred embodiment, the promoter includes the nucleotide sequence from approximately nucleotide −1142 to nucleotide +26 of SEQ ID NO:1 (FIG. 2), which sequence contains genetic elements functional in the transcription and translation of operably attached genetic sequences. An embodiment of the invention further includes sequences in the region 3' of the coding sequence, preferably from nucleotide +1165 (immediately 3' of the stop codon) to nucleotide +1606 (3' of the poly(A) signal) (FIG. 2). Intronic sequences (FIG. 2) containing functional genetic elements of the melatonin 1a receptor gene are a further embodiment of the instant invention. Such functional genetic elements include, but are not limited to, enhancers, response elements, cis and/or trans acting factor binding sites, and the like.

In preferred embodiments of the screening methods, by operable attachment of the recombinant high-affinity melatonin receptor gene promoter to a gene of interest, the gene of interest is stably expressed by a mammalian cell which does not normally express the gene of interest. The gene of interest may be any gene expressible in a cell and whose transcription is detected after introduction into a cell. Preferred genes of interest are reporter genes which include, but are not limited to, the coding sequence for β-galactosidase, antibiotic resistance genes, SV40 T antigen, chloramphenicol acetyltransferase (CAT), human growth hormone (hGH), and the like.

By "transcriptional regulatory regions" or "transcriptional regulatory sequences" or "promoter" is meant nucleic acid sequences upstream and downstream of the coding region of a melatonin 1a receptor gene, which sequences function in the initiation of transcription of the coding region into mRNA and encode sequences functional in translation of the mRNA into the amino acid sequence of the high-affinity melatonin receptor polypeptide. The transcriptional regulatory sequences are the minimal sequences sufficient to direct transcription. Also included in the invention are those promoter elements which are sufficient to render promoter-dependent gene expression controllable for cell-type specific, tissue-specific or inducible by external signals or agents; such elements may be located in the 5' or 3' regions of the native gene.

By "reporter gene" is meant a gene whose expression may be assayed; such genes include, without limitation, luciferase, β-galactosidase, and chloramphenicol transacetylase (CAT).

By "operably linked" is meant that a gene and a regulatory sequence(s) are connected in such a way as to permit gene expression when the appropriate molecules (e.g., transcriptional activator proteins) are bound to the regulatory sequence(s).

By "positioned for expression" is meant that the DNA molecule is positioned adjacent to a DNA sequence which directs transcription and translation of the sequence (i.e., facilitates the production of, e.g., a recombinant protein or a RNA molecule).

By "high-affinity melatonin receptor polypeptide" is meant all or part of a vertebrate cell surface protein which specifically binds melatonin and signals the appropriate melatonin-mediated cascade of biological events (e.g., a decrease in intracellular cAMP) concentration. The polypeptide is characterized as having the ligand binding properties (including the agonist and antagonist binding properties) and tissue distribution described herein.

By a "polypeptide" is meant any chain of amino acids, regardless of length or post-translational modification (e.g., glycosylation).

By a "substantially identical" nucleic acid sequence is meant a nucleic acid sequence which differs by less than 10%, preferably less than 5% of nucleic acids of the transcriptional regulatory regions of the melatonin 1a receptor gene. Preferably, a substantially identical nucleic acid sequence of the transcriptional regulatory regions are functional initiating transcription at substantially the same frequency as the regulatory regions of SEQ ID NO:1, preferably at a frequency of at least 50%, more preferably 80% of the frequency initiated by the regulatory regions of SEQ ID NO:1. The nucleic acid sequence of SEQ ID NO:1 or a substantially identical sequence may be isolated from a vertebrate animal or may be chemically synthesized by standard techniques.

By "derived from" is meant encoded by the genome of that organism and present on the surface of a subset of that organism's cells.

By "isolated DNA" is meant a DNA that is not immediately contiguous with (i.e., covalently linked to) both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of genetic engineering, a DNA molecule encoding the transcriptional regulatory regions of a high-affinity melatonin receptor (or a fragment or analog, thereof). Such a DNA molecule is "positioned for expression" meaning that the DNA molecule is positioned adjacent to a DNA sequence and directs transcription and translation of the sequence (i.e., facilitates the production of genetic transcript and/or protein of interest, or fragment or analog, thereof).

A "transgenic animal" as used herein denotes an animal (such as a non-human mammal) bearing in some or all of its nucleated cells one or more genes derived from a different species (exogenous); if the cells bearing the exogenous gene include cells of the animalls germline, the gene may be transmissible to the animal's offspring. As used herein, genes derived from a different species of animal are exogenous genes. Preferably the exogenous genes include nucleotide sequences which effect expression of the gene in its endogenous tissue distribution.

The melatonin 1a receptor transcriptional regulatory regions of the invention control the expression of melatonin 1a, a receptor likely to be involved in the function of vertebrate circadian rhythm. Such transcriptional regulatory regions are therefore useful to develop therapeutics to treat such conditions as jet lag, facilitate reentrainment of some endogenous melatonin rhythms, synchronize the disturbed sleep-wake cycle of blind people, alleviate sleep disorders in shift workers, facilitate the emergence of a diurnal sleep-wake pattern in neonates, regulate ovarian cyclicity in human females, control the initiation and timing of puberty in humans, and alter the mating cycle in seasonally breeding animals, such as sheep. Preferred therapeutics include 1) transcriptional activators, e.g., compounds which increase transcription of an operably attached gene of interest through interaction with the high affinity melatonin receptor gene promoter of the invention; and 2) transcriptional inactivators, e.g., compounds which block high-affinity melatonin receptor gene promoter function by interfering with the transcriptional activator:promoter interaction.

Because the receptor gene promoter component may now be produced by recombinant techniques and because candidate compounds may be screened using transformed, cultured cells, the instant invention provides a simple and rapid approach to the identification of useful therapeutics. Such an approach was previously difficult because of the localization of the receptor and its genetic regulatory regions to a few discrete regions in the central nervous system of most mammals. Isolation of the high-affinity melatonin receptor transcriptional regulatory regions allows expression of a gene of interest in a cell type which does not normally express the gene of interest, providing a system for assaying a melatonin 1a receptor transcriptional activator or inhibitor.

Other features and advantages of the invention will be apparent from the following description of the preferred embodiments thereof, and from the claims.

DETAILED DESCRIPTION

The drawings will first briefly be described.

DRAWINGS

Figure 1:
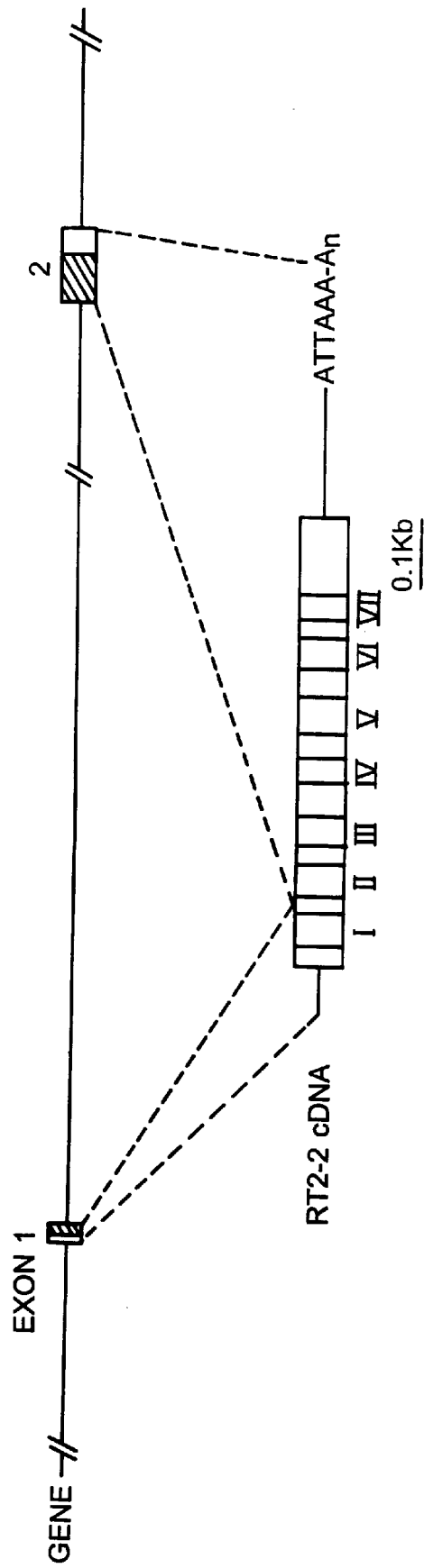

FIG. 1 is a schematic representation of the structure of the mouse $Mel_{1a}$ melatonin receptor gene. The genomic map shows the receptor gene with exons depicted as bars. Translated regions of the exons are black bars, while the 5' and 3' untranslated regions are open bars. Below the gene, the receptor cDNA is shown with the coding region depicted as a wide bar; transmembrane domains I to VII are indicated. The thin lines depict the untranslated regions. Dashed lines between the gene and cDNA show the portions of the gene encoding the cDNA.

Figure 2A:
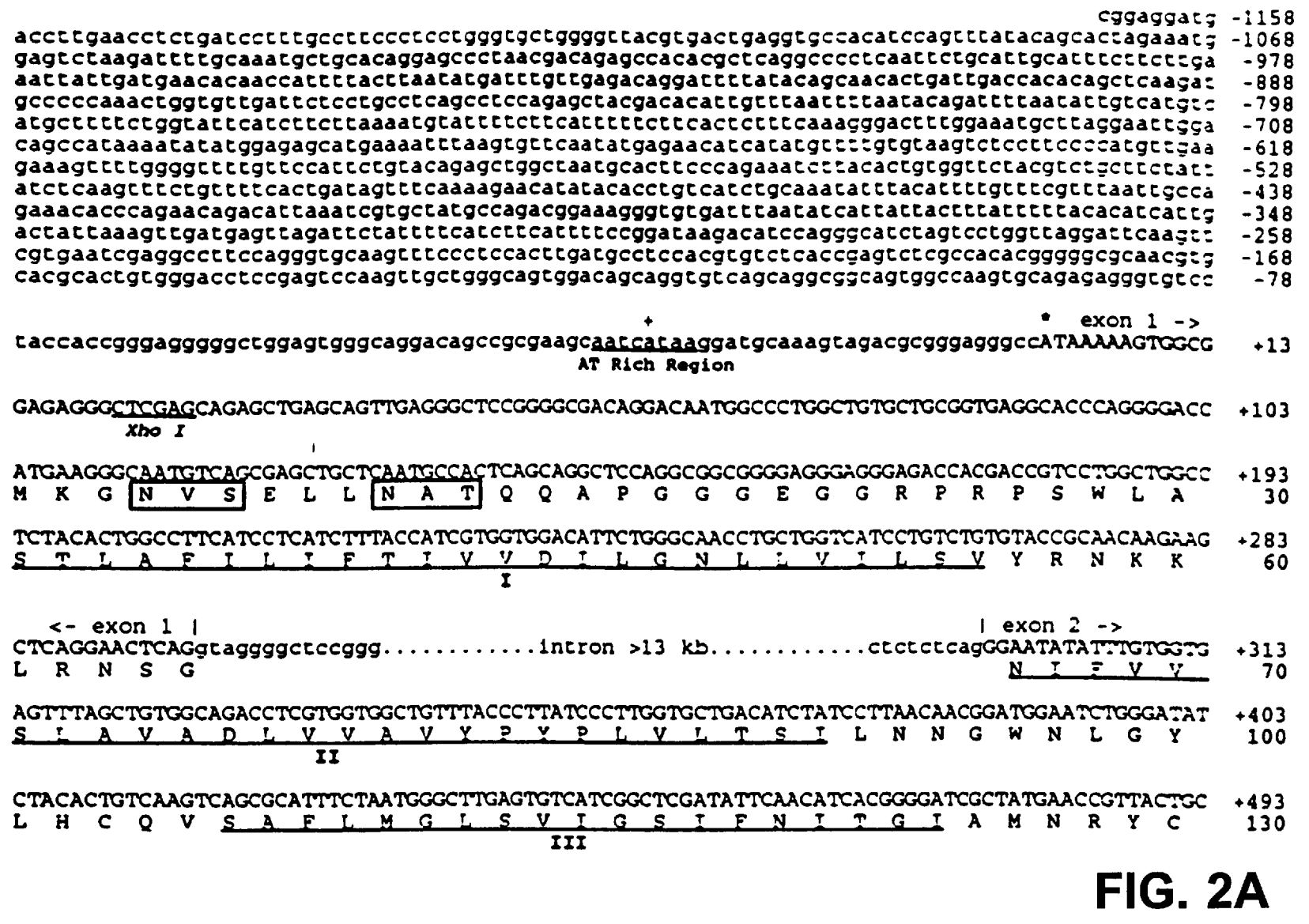

FIGS. 2A and 2B are digrams is a diagram of the nucleotide sequence of the mouse $Mel_{1a}$ receptor gene. Nucleotide sequence is numbered from the major transcription start site which defines the start of the first exon. In the coding region, consensus sites for N-linked glycosylation (box) and protein kinase C phosphorylation (oval) are indicated and the transmembrane regions are underlined. In the 3' untranslated region, an ATTTA sequence (bold print) and consensus sequence for a polyadenylation signal (underlined) are highlighted. The nucleotide and amino acid numbers are to the right of each line. The sequence has been deposited in GenBank under accession number U52222.

Figure 3A:
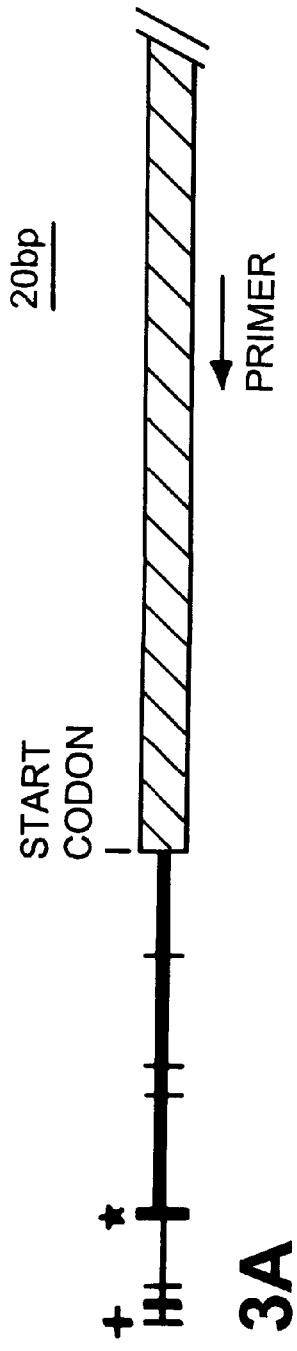
Figure 3B:
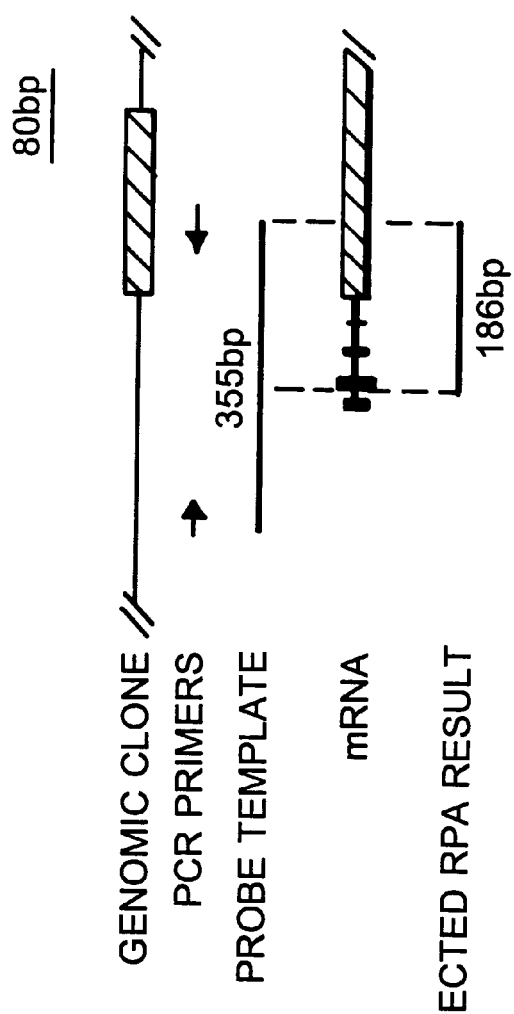

FIGS. 3A and 3B are diagrams of strategies for determining the transcription start sites of the mouse $Mel_{1a}$ receptor gene. A. 5'-RACE analysis was used to clone upstream sequences. After reverse transcription, PCR amplification was performed using a primer in the amino terminus and a 5' anchor primer. The vertical lines depict the location of 15 clones sequenced. The star (*) denotes 6 clones that ended 103 nucleotides upstream of the translation start codon; + denotes 2 clones that ended 133 nucleotides upstream of the translation start codon. B. RNase protection analysis was used to further define the transcription start site. The cRNA probe (335 nucleotides in length) and protected fragment (186 base pairs in length) are shown.

Figure 4:
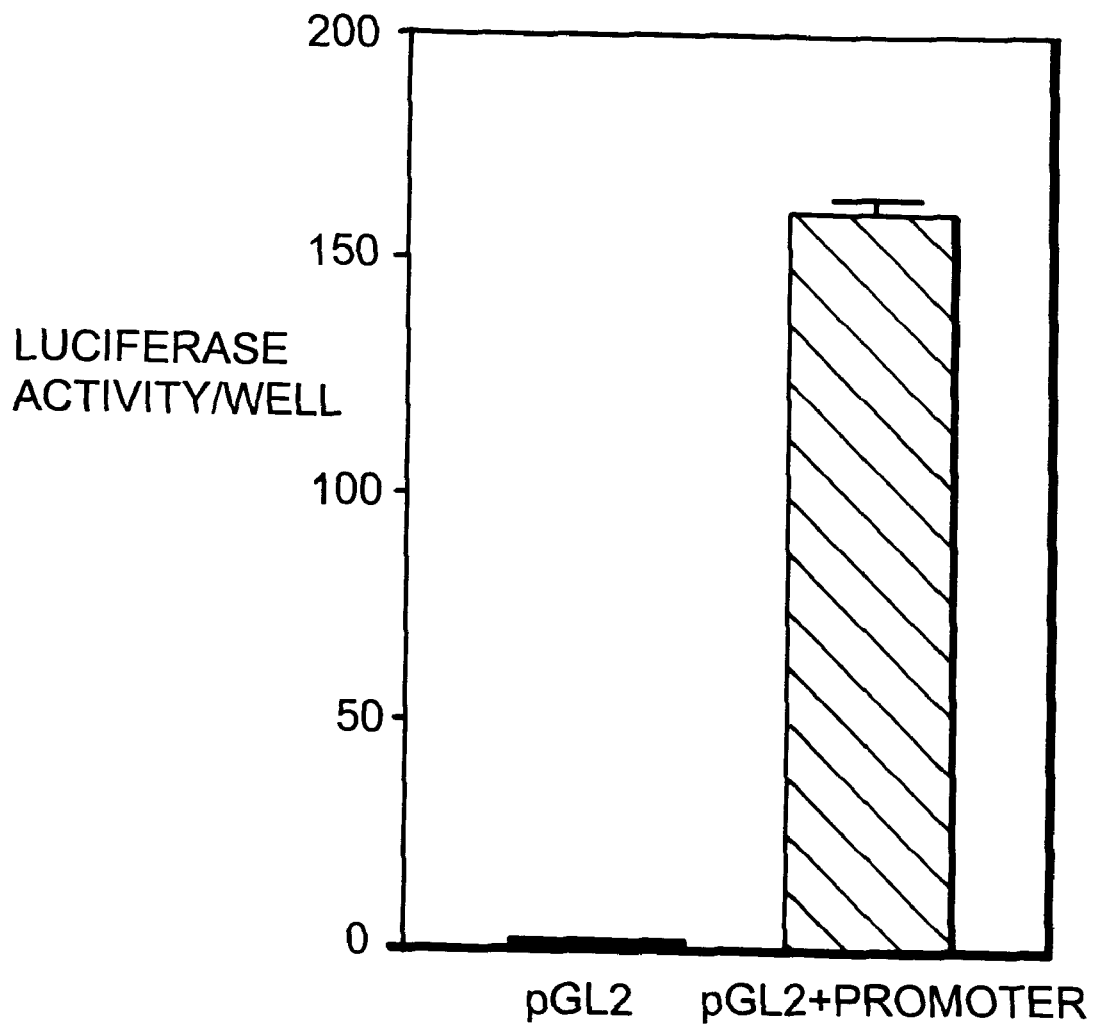

FIG. 4 is a bar graph showing that the 5' flanking region of the mouse $Mel_{1a}$ receptor gene functions as a promoter in RT2-2 cells. RT2-2 cells were transfected with a pGL2-Basic luciferase reporter vector containing 1.1 kb of the 5' flanking region or the pGL2 vector without the insert. Results are mean ± SEM of four independent experiments.

EXAMPLES

There now follows a description of the cloning and characterization of the high-affinity melatonin 1a receptor transcriptional regulatory regions from mouse. Transformed cells containing and expressing DNA operably attached to the transcriptional regions of mouse melatonin 1a receptor are also described. These examples are provided for the purpose of illustrating the invention, and should not be construed as limiting.

Example 1
Molecular Cloning of Transcriptional Regulatory Regions from Mouse Melatonin 1a Receptor A 466 bp fragment of the mouse $Mel_{1a}$ melatonin receptor gene was cloned from genomic DNA by PCR. Genomic DNA or first strand cDNA underwent 30–35 cycles of amplification by PCR using two oligonucleotide primers (200 nM final concentration). Each reaction cycle consisted of incubation at 94° C. for 45 sec, 45° C. for 2 min (for degenerate primers) or 60° C. for 2 min (for specific primers), and 72° C. for 2 min, with AmpliTaq DNA Polymerase (Perkin-Elmer Cetus, Foster City Calif.). Amplified DNA was separated on an agarose gel and paper-eluted as previously described (Reppert, S. M. et al. (1994) *Neuron* 13:1177–1185). The DNA was then subcloned into PCRII using a TA cloning kit (Invitrogen, San Diego Calif.), or digested with restriction enzymes and subcloned into pBluescriptII SK+ or KS+ (Stratagene, La Jolla Calif.).

PCR was performed using degenerate oligonucleotide primers based on amino acid residues in the third and seventh transmembrane domains conserved among the previously cloned mammalian $Mel_{1a}$ receptors (see, for example, U.S. application Ser. No. 08/466,103, incorporated herein by reference in its entirety). Polymerase chain reaction (PCR) of mouse genomic DNA yielded a 466 bp fragment that was 94% identical at the amino acid level to the rat and Djungarian hamster $Mel_{1a}$ receptor cDNAs.

The PCR-generated fragment of the mouse $Mel_{1a}$ receptor was used to probe a mouse genomic library. A BALB/c adult mouse liver EMBL3 SP6/T7 genomic library (Clontech, Palo Alto Calif.) was plated (12 plates; 100,000 pfu/plate) and transferred to Colony Plaque Screen filters (New England Nuclear, Boston Mass.). The filters were screened under conditions of either high or reduced stringency as previously described (Reppert, S. M. et al. (1994) supra). Probes were cDNA fragments labeled with [alpha-$^{32}$P]dCTP (3000 Ci/mmol) by the method of random priming (Pharmacia, Piscataway N.J.). Phage that hybridized to probe were plaque-purified.

Ten positively hybridizing clones were isolated and plaque-purified. In the sheep and human $Mel_{1a}$ receptor genes, there is an intron in the region coding the first intracellular loop. Thus, the genomic library was reprobed with a 160 bp fragment of the coding region of the sheep $Mel_{1a}$ receptor immediately upstream from the GN motif that resides in the first cytoplasmic loop (Reppert, S. M. et al. (1994) *Neuron* 13:1177–1185). The sheep fragment hybridized to a separate population of ten clones. These clones did not overlap with the clones found using the mouse fragment, suggesting the presence of a large intron. Both sets of phage clones were mapped by restriction endonucleases, and PCR and Southern analyses. Selected genomic fragments were subcloned and sequenced by standard techniques.

Comparison of the genomic sequence with the coding and untranslated regions of the cDNA showed that the mouse $Mel_{1a}$ receptor gene is composed of two exons. Exon 1 encodes the entire 5' untranslated region and the coding region through the first cytoplasmic loop (see FIG. 1). Exon 2 encodes the rest of the coding region and the entire 3'-untranslated region. Based on restriction endonuclease mapping of genomic clones, the intron length is greater than 13 kb. The intron has conserved 5' GT-AG 3' sequence for splicing. Previous studies have shown that the mouse $Mel_{1a}$ receptor gene (Mtnr1a) is a single copy gene and resides on chromosome 8 (Slaugenhaupt, S. A. et al. (1994) *Genomics* 27:355–357).

Example 2
Expression of Melatonin 1a Receytor Gene in Mammalian Cells

Based on studies in rats and hamsters, $Mel_{1a}$ melatonin receptor mRNA is expressed at low levels with limited distribution in brain (Reppert, S. M. et al. (1994) *Neuron* 13:1177–1185). A vertebrate cell line expressing the $Mel_{1a}$ receptor was sought for analysis of the 5'- and 3'-untranslated regions of the receptor DNA. RT2-2 cells are a cell line of immortalized retinal amacrine cells derived from SV40 T antigen-induced tumors in transgenic mice (Hammang, J. P. et al. (1990) *Neuron* 4:775–782; RT2-2 cells were provided by C. Mahle, Bristol-Myers Squibb, New Jersey). RT2-2 cells bind melatonin with high affinity ($K_d$=50 to 100 pM) and modest capacity ($B_{max}$ 20 to 40 fmol/mg protein) suggesting that these cells express a high-affinity melatonin receptor (Mahle, C. D. et al. (1994) Abstract, *Program of the 24th Annual Meeting of The Society for Neuroscience*, Miami, Fla., p. 535).

RNA extraction from RT2-2 cells was performed as follows. RT2-2 cells were grown as a monolayer at 37° C. in 5% $CO_2$ in OPTI-MEM I (GIBCO/BRL, Grand Island N.Y.) with 10% heat-inactivated fetal calf serum. Total RNA was extracted from RT2-2 cells using an acid-phenol method (Chomczynski, P., and Sacchi, N. (1987) *Anal. Biochem* 162:156–159). Poly(A)$^+$ RNA was prepared as previously described (Reppert, S. M. et al. (1991) *Mol. Endocrinol.* 5:1037–1048). Abundant mRNA for the $Mel_{1a}$ receptor was identified in RT2-2 cells by RNase protection analysis using the PCR-generated receptor fragment.

Sequence analysis of two sets of clones from the mouse genomic library delineated the apparent 5' and 3' ends of the coding region. RT-PCR of MRNA from RT2-2 cells using specific primers flanking the 5' and 3' ends of the coding region amplified the expected cDNA with the intron spliced out at the predicted splice sites. The PCR-generated cDNA was subcloned into pcDNA3 for sequence analysis and in situ hybridization.

The mouse $Mel_{1a}$ receptor encodes a protein of 353 amino acids and has structural features characteristic of the melatonin receptor family (see applicant's related U.S. application Ser. No. 08/466,103). These include an NRY motif just downstream from the third transmembrane domain, a C(C/Y)ICH motif immediately downstream from NRY and an NAXXY motif in transmembrane 7. Overall, the coding region of the mouse receptor is 83% and 85% identical at the amino acid level with the sheep and human $Mel_{1a}$ receptors, respectively; the sheep and human receptors are the only other members of this subtype in mammals in which the full length coding region has been cloned, sequenced, and expressed (U.S. application Ser. No. 08/466,103; and Reppert, S. M. et al. (1994) *Neuron*, supra). The mouse $Mel_{1a}$ receptor has 2 consensus sites for N-linked glycosylation in the amino terminus. The second cytoplasmic loop contains two consensus sites for protein kinase C phosphorylation that may be involved in receptor regulation. The carboxyl tail also has several serine residues that might serve as phosphorylation sites.

Example 3
Analysis of the Mouse Melatonin 1a Receptor Gene 5' Untranslated Region Transcription start sites for the $Mel_{1a}$ receptor gene were examined using 5'-RACE. 5'-RACE was performed using the 5'-AmpliFINDER RACE Kit (Clontech). First strand cDNA was generated by reverse transcription of poly(A)$^+$ RNA from RT2-2 cells using a primer corresponding to a nucleotide sequence in transmembrane 1 of the mouse $Mel_{1a}$ melatonin receptor. The AmpliFINDER anchor was ligated to the cDNA ends using T4 RNA ligase. The cDNA was then amplified using an anchor primer (complementary to the AmpliFINDER anchor) and a primer nested immediately upstream of the primer used for reverse transcription. The amplified cDNA was separated on an agarose gel. Specific bands were paper eluted, subcloned into pCRII, and sequenced.

Primer 5'-GTACACAGACAGGATGACCAGCAG-3' (SEQ ID NO:3) corresponding to +248 to +271 in transmembrane 1 was used for reverse transcription, while primer 5'-CAGCAGGTTGCCCAGAATGTCCACCAC-3' (SEQ ID NO:4), which nested just upstream at +227 to +253, was used for PCR amplification. Sequence analysis of the 5'-RACE clones indicated the presence of multiple potential start sites (FIG. 3A). In the 5'-untranslated region, the cDNA sequence matched the genomic sequence, indicating that introns were not present. Of 15 clones sequenced, 6 ended 103 bp upstream of the translation start codon suggesting that this was the major transcription start site. The two longest cDNAs extended 133 bp upstream of the translation start codon (FIG. 3A).

To verify the 5'-RACE results, RNase protection analysis was performed using a 335 bp fragment generated by PCR using primers derived from the $mel_{1a}$ genomic sequence (FIG. 3B). One primer (5'-TTCAAGCTTAGCCAGGACGGTCGTGGTCTCCCT-3' (SEQ ID NO:5)) corresponded to +166 to +189 in the amino terminus. The other primer (5'-TCAGAATTCGAGTCCAAGTTGCTGGGCAGTGGA-3' (SEQ ID NO:6)) was 125 to 149 nucleotides upstream of the putative transcription start site suggested by 5'-RACE analysis. The resulting fragment was subcloned and linearized to generate a CRNA probe. The probe was made with $^{32}$p-UTP (up to 6000 Ci/mmol) using the MAXIscript system (Ambion, Austin Tex.). Ribonuclease protection assays were run using the RPAII system (Ambion), as previously described (Reppert, S. M. et al. (1994) *Neuron* 13:1167–1176). Total RNA or poly(A)$^+$ RNA was mixed with approximately 10$^5$ cpm of each probe in a 20 ml volume of hybridization buffer. Hybridization mixtures were heated to 95° C. for 3 min and then incubated at 45° C. overnight. Unhybridized RNA was digested by a RNase A/RNase T1 mixture for 1 hr at 37° C. Samples were boiled and separated on 8M urea/5% acrylamide gels. For all RNase protection analyses, control samples were run using yeast RNA, sense probes, and omission of RNase.

RNase protection analysis results confirmed that the predominant transcription start site was 103 bp upstream of the translation start codon, with minor sites to 133 bp upstream. Sequencing of the cloned 5' upstream region was performed by standard techniques.

Sequence analysis of 1.1 kb of the 5' flanking region revealed that it did not contain typical TATA or CAAT boxes in the region of the transcription start sites (FIG. 2). However, there was an AT rich region at −27 to −34 nucleotides. No consensus binding sequences for cAMP regulatory elements were identified in the sequenced region.

To establish that this region functioned as a promoter, a 1.1 kb fragment of the 5' flanking region, corresponding to the region −1132 to +26 relative to the transcription start site (see FIG. 2), was subcloned into the pGL2-Basic luciferase reporter vector (Promega, Madison Wis.) by standard techniques. The insert-containing vector or vector without insert was transfected into RT2-2 cells (2 μg cDNA/35 mm well) using a modified diethylaminoethyl dextran method (Cullen, B. R. (1987) *Methods Enzymol.* 152:684–704). Two days after transfection, cell lysates were harvested with Reporter Lysis Buffer (Promega). Luciferase activity in lysates was measured by a Luminoskan luminometer (Labsystems, Helsinki) (dewet, J. R. et al. (1987) *Mol. Cell. Biol.* 7:725–737). For each cDNA construct, triplicate 35 mm wells were assayed in duplicate. Consistent transfection efficiency was verified by cotransfection with a pCMV-β-galactosidase vector in preliminary studies (Rosenthal, N. (1987) *Methods Enzymol.* 152:704–720). As a positive control, parallel plates were transfected with pCMV-luciferase in each experiment (Treacy, M. N. et al. (1991) *Nature* 350:577–584).

Luciferase activity in RT2-2 cells transfected with the 5' flanking/pGL2 construct was 160±3.4 (mean±SEM), while luciferase activity was 1.4±0.4 in RT2-2 cells transfected with the pGL2 vector lacking insert (FIG. 4). Thus, the 1.1 kb flanking region of the mouse receptor gene caused a mean 114-fold induction of luciferase activity over control (vector alone) values. This showed that the 5' flanking region immediately upstream of the transcription start site from approximately nucleotide −1132 to nucleotide +62 relative to the transcription start site (FIG. 2) acts as a functional promoter in RT2-2 cells.

A TATA box is not present in the mouse receptor gene promoter to position RNA polymerase II for the initiation of transcription. Lack of a TATA sequence is common among genes possessing several transcription start sites, as is the case for the mouse $Mel_{1a}$ receptor gene. Indeed, many G-protein coupled receptor genes are likewise missing a TATA box in their promoters, including genes for luteinizing hormone (Tsai-Morris, C. H. et al. (1991) *J. Biol. Chem.* 266:11355–11359), follicle-stimulating hormone (Heckert, L. L. et al. (1992) *Molecular Endocrinology* 6:70–80), thyrotropin (Ikuyama, S. et al. (1992) *Molecular Endocrinology* 6:793–804), gonadotropin-releasing hormone (Albarracin, C. T. et al. (1994) *Endocrinology* 135:2300–2306), and oxytocin (Rozen, F. (1995) *Proc. Natl. Acad. Sci. USA* 92:200–204) receptors; multiple start sites are found in the genes for all of these receptors. In the mouse $Mel_{1a}$ receptor gene promoter, an AT-rich region which may be involved in the initiation of transcription (Hahn, S. et al. (1989) *Proc. Natl. Acad. Sci. USA* 86:5718–5722; Singer, V. L. et al. (1990) *Genes and Development* 4:636–645; and Wobbe, C. R. and Struhl, K. (1990) *Molecular and Cellular Biology* 10:3859–3867) is located 27 to 34 nt upstream of the major cap site. GC-rich regions, which often surround a TATA box, surround this AT-rich region. The GC content of the first 200 bases upstream of the major transcription start site is 65%, similar to that reported for other G protein-coupled receptor genes (Ikuyama, S. et al. (1992) supra). However, there are no canonical GC or CAAT boxes present in the mouse $mel_{1a}$ receptor gene promoter.

A functional promoter was shown to be present in the 1.1 kb 5' flanking region of the mouse $Mel_{1a}$ receptor gene. The 114-fold increase in luciferase activity in RT2-2 cells transfected with vector containing the $Mel_{1a}$ receptor gene promoter compared to cells transfected with a promoterless reporter vector showed that the promoter was functional in RT2-2 cells.

The sequence of the 5' flanking region of the mouse $Mel_{1a}$ receptor gene was analyzed for elements involved in regulation of transcription. The GCG (Genetics Computer Group, Madison Wis.) Wisconsin Package MAP command was utilized with the data file tfsites.dat, defined by the logical name genmoredata.

Example 4

Analysis of the 3' Untranslated Region of Mouse Melatonin 1a Receptor Gene

The length of the 3' untranslated region was determined by 3'-RACE using two rounds of PCR amplification. 3'-RACE was performed using the 3'-RACE System (GIBCO/BRL, Bethesda Md.). First strand cDNA was generated using an Adapter Primer which is an oligo(dT) primer engineered to contain three restriction endonuclease sites at the 5' end. The cDNA was then amplified by PCR using an Anchor Primer complementary to the specific 5' sequence of the Adapter Primer and a primer corresponding to nucleotide sequence in transmembrane 6 of the mouse $mel_{1a}$ receptor. A second amplification step used the Anchor Primer and a primer nested in transmembrane 7 downstream of the one used in the first amplification. The cDNA of the second amplification was separated on an agarose gel. A single band was paper eluted, subcloned into pCRII, and sequenced.

The first round of amplification used primer 5'-ACTCAACCTCATAGGTCTTATTGT-3' (SEQ ID NO:7) corresponding to +871 to +894 in transmembrane 6, while the second round used primer 5' CCAGAGTGGCTGT-TCGTGGCTAGT 3' (SEQ ID NO:8) nested downstream at +929 to +952 in transmembrane 7 (FIG. 2). Sequence analysis of 3'-RACE clones consistently revealed a 650 bp cDNA fragment which included 444 bp of the 3' untranslated region ending with a poly(A) tail. The fragment contained an ATTTA sequence that may be involved in regulating mRNA stability (Sachs, A. B. (1993) *Cell* 74:413–421) and the polyadenylation consensus sequence ATTAAA 18 bp before the start of the poly(A) tail (FIG. 2). The 3' untranslated sequence matched the sequence found in genomic DNA downstream of the coding region, indicating that introns are not present in the 3' untranslated region.

The 3' untranslated regions of genes are believed to be involved in mRNA stability, and may contain sequences that regulate gene activity (Jackson, R. J. and Standart, N. (1990) *Cell* 62:15–24). Thus, it is noteworthy that the 3' untranslated region of the mouse $Mel_{1a}$ receptor gene contains an AU-rich element (ATTTA). This element can induce mRNA instability (Sachs, A. B. (1993) supra), suggesting that the mouse $Mel_{1a}$ receptor transcript might be unstable and short-lived. Deletion or alteration of the AU-rich element to alter $Mel_{1a}$ receptor transcript stability is within the scope of the invention for increasing expression of $Mel_{1a}$.

Example 5
Tissue Distribution of Mouse Melatonin 1a Receyter Gene Expression

Northern blot analysis of RNA from RT2-2 cells confirmed the RNase protection analysis result that the $Mel_{1a}$ receptor was expressed moderately in these cells. Hybridization of the blot with the PCR-generated $Mel_{1a}$ probe from exon 2 revealed two transcripts: an intense hybridization signal at approximately 1.8 kb and a much weaker signal at approximately 7 kb relative to transcript size standards. No hybridization signal was detected in whole mouse brain.

In rats and hamsters, the $Mel_{1a}$ melatonin receptor transcript has been identified in PT and SCN (Reppert, S. M. et al. (1994) *Neuron*, supra). The distribution of $mel_{1a}$ receptor mRNA was examined in the mouse SCN and pituitary by in situ hybridization using a cRNA probe complementary to the entire coding region. $^{35}$S-labeled antisense cRNA probes were generated by HindIII digestion of pCDNA3 containing the entire coding region of the mouse receptor, followed by in vitro transcription with SP6 RNA polymerase (Ambion) in the presence of [$^{35}$S]alpha-thio-UTP (New England Nuclear; 1100–1200 ci/mmol) as previously described (Reppert, S. M. (1991) *Mol. Endocrinol.* 5:1037–1048). As a control, sense CRNA probes were generated from each plasmid and processed along with the antisense probes. In addition to the distribution of $Mel_{1a}$ receptor mRNA in mouse SCN and pituitary, the distribution of high-affinity melatonin binding sites was examined on adjacent sections by in vitro autoradiography using $^{125}$I-Mel.

The highest level of receptor MRNA was found in mouse PT. The SCN of adult mice also displayed a moderate hybridization signal. Intense $^{125}$I-Mel binding was found in both PT and SCN. In situ hybridization analysis of the SCN in newborn mice showed an intense hybridization signal in SCN and a diffuse signal in lateral hypothalamus. Examination of emulsion autoradiograms from these animals showed that the hybridization signal was more intense in the ventral SCN. Within this region, only scattered cells displayed silver grains. There was no obvious day-night difference in hybridization intensity in the adult SCN.

Example 6
Expression of an Exogenous Gene from a Vertebrate Melatonin 1a Receptor Gene Promoter An expression cassette, genetic construct, or expression vector containing a gene of interest (such as a reporter gene) operably linked to the transcriptional regulatory regions of a vertebrate $Mel_{1a}$ receptor gene promoter (such as from a mouse) according to the invention may be expressed by transformation of a suitable host cell.

Those skilled in the field of molecular biology will understand that any of a wide variety of expression systems may be used to provide the recombinant expression construct. The precise host cell used is not critical to the invention provided the host cell expresses DNA operably linked to the mouse $Mel_{1a}$ receptor gene promoter. A host cell useful for the expression from the mouse $Mel_{1a}$ receptor gene promoter is the RT2-2 cell (Bristol-Myers Squibb, New Jersey). The method of transfection and the choice of expression vehicle will depend on the host system selected. Transformation and mammalian cell transfection methods are described, e.g., in Ausubel et al. (*Current Protocols in Molecular Biology*, John Wiley & Sons, New York, (1989)); expression vehicles may be chosen from those provided, e.g., in *Cloning Vectors: A Laboratory Manual* (Pouwels, P. H. et al., (1985), Supp. 1987).

One particularly preferred expression system is the RT2-2 cell transfected with a pGL2-Basic luciferase vector containing the 1.1 kb 5' flanking sequence from −1132 to +26 bp upstream of the transcription start site of the mouse $Mel_{1a}$ receptor gene as described above. DNA encoding the mouse $Mel_{1a}$ receptor gene promoter was inserted into the pGL2-Basic luciferase vector in an orientation designed to allow expression of luciferase. The expression construct may be used in a screening method of the invention.

Alternatively, the mouse $Mel_{1a}$ receptor gene promoter-:reporter gene construct is expressed by a stably-transfected mammalian cell line.

A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the $Mel_{1a}$ promoter:reporter gene construct is cloned into an expression vector which includes a promoterless second reporter gene. Such a construct allows integration of the plasmid and, therefore, the $Mel_{1a}$ promoter:reporter gene construct into the host cell chromosome to be selected for, such as by inclusion of a substrate for the second reporter gene (as described in Ausubel et al., supra). This dominant selection can be accomplished in most cell types.

Expression of a $Mel_{1a}$ promoter:reporter gene (e.g., produced by any of the expression systems described herein) may be assayed by immunological procedures, such as Western blot or immunoprecipitation analysis of recombinant cell extracts, or by immunofluorescence of intact recombinant cells (using, e.g, the methods described in Ausubel et al., supra); by light emission assays (using, e.g., luciferase as described herein); by colorimetric assay (using, e.g., β-galactosidase expression), for example.

Example 7
Screening For Melatonin 1a Receptor Gene Promoter Activators and Inhibitors As discussed above, one aspect of the invention features screening for compounds that activate transcription from the mouse $Mel_{1a}$ receptor gene transcriptional regulatory sequences, thereby inducing an increase in the amount of $Mel_{1a}$ receptor expressed cells of the SCN and PT, and in turn increasing sensitivity to circulating melatonin. An element of the screen is recombinant $Mel_{1a}$ receptor gene promoter:reporter gene transfected into a cell allowing expression of the $Mel_{1a}$ receptor gene promoter (such as RT2-2 cells). Preferably, the $Mel_{1a}$ receptor gene promoter is from a vertebrate animal such as a mouse. Other elements of the screen include contacting the transfected cell with a candidate compound and monitoring an increase in reporter gene activity as indicative of increased expression from the $Mel_{1a}$ receptor gene promoter.

A screen for a compound capable of inhibiting $Mel_{1a}$ receptor gene promoter function is screened in the same manner as described for transcription activators except that a decrease in reporter gene activity is monitored.

Preferably, such screening assays are carried out using a cell line (such as RT2-2) stably transfected with the $Mel_{1a}$ receptor gene promoter:reporter gene construct. Most preferably, the untransfected cell line expresses substantially no reporter gene.

Transcriptional activators may be expected to be a useful therapeutic agent for circadian rhythm disorders such as jet lag, day/night cycle disorders in humans or mating cycle alterations in animals such as sheep by increasing the number of melatonin receptors on the surface of cells in the SCN or PT and thereby increasing the sensitivity of the animal to circulating melatonin.

Transcriptional inhibitors may be expected to be a useful therapeutic agent for disorders treatable by decreasing the number of melatonin receptors on the surface of SCN or PT cells thereby decreasing the sensitivity of the animal to melatonin. Such disorders include, but are not limited to, controlling reproductive cycles in mammals, such as controlling the initiation of timing of puberty in humans.

Example 8
Preparation of a Transgenic Animal Containing a Recombinant Melatonin 1a Regulatory Seguence:Reporter Gene Cassette There are several means by which transgenic animals can be made. A transgenic animal (such as a mammal) may be constructed by one of several techniques, including targeted insertion of an exogenous melatonin receptor gene into the endogenous gene of the animal, or other methods well known to those skilled in the art.

A transgenic mammal whose germ cells and somatic cells contain an exogenous reporter gene under the control of a melatonin receptor gene transcriptional regulatory region is produced by methods known in the art. See, for example, U.S. Pat. No. 4,736,866 describing production of a transgenic mammal, herein incorporated by reference in its entirety. Generally, the DNA sequence encoding an exogenous melatonin 1a receptor gene promoter operably linked to a reporter gene of interest is introduced into the animal, or an ancestor of the animal, at an embryonic stage (preferably the one-cell, or fertilized oocyte, stage, and generally not later than about the 8-cell stage). There are several methods known to the art of introducing a foreign gene into an animal embryo to achieve stable expression of the foreign gene. One method is to transfect the embryo with the gene as it occurs naturally, and select transgenic animals in which the foreign gene has integrated into the genome at a locus which results in its expression. Other methods involve modifying the foreign gene or its control sequences prior to introduction into the embryo.

Tissues of transgenic mammals are analyzed for the presence of exogenous reporter gene product, either by directly analyzing mRNA, or by assaying the tissue for exogenous product.

Example 9
Using the Transgenic Mammal to Determine Melatonin Receptor Gene Promoter Activation or Inhibition The animals described above can be used to determine whether candidate compounds are melatonin promoter activators or inhibitors in vivo.

One aspect of the invention features screening for compounds that agonize or antagonize melatonin activity in vivo. The elements of the screen are a $Mel_{1a}$ promoter:reporter gene transgenic mammal and a potential melatonin 1a receptor gene promoter activator or inhibitor in a suitable formulation for administration to the mammal. Detection of a change in the phenotype of interest (e.g., sleep/wake cycle or reproductive cycle) relative to a control transgenic mammal to which no promoter activator or inhibitor has been administered indicates a potentially useful candidate compound.

Therapy

Particularly suitable therapeutics for the treatment of circadian rhythm disorders in humans as well as for regulating changes in the reproductive cycle of seasonally breeding animals are the transcriptional activators and inhibitors described above formulated in an appropriate buffer such as physiological saline.

The therapeutic preparation is administered in accordance with the condition to be treated. ordinarily, it will be administered intravenously, at a dosage, of a duration, and with the appropriate timing to elicit the desired response. Appropriate timing refers to the time in the natural circadian rhythm at which administration of therapeutic preparation elicits the desired response. Alternatively, it may be convenient to administer the therapeutic orally, nasally, or topically, e.g., as a liquid or a spray. Again, the dosages are as described above. Treatment may be repeated as necessary for alleviation of disease symptoms.

Melatonin 1a receptor gene promoter transcriptional activators can be used to reentrain the endogenous melatonin rhythm of humans; alleviate jet lag symptoms in humans; phase shift the sleep/wake cycle of some blind people, reinforce entrainment of endogenous melatonin rhythm using low intensity light/dark cycle; control ovulation in humans; and alter reproductive cycles in seasonally breeding animals.

Melatonin 1a receptor gene promoter transcriptional inhibitors may be useful in controlling reproductive cycles in mammals, such as controlling the initiation or timing of puberty in humans.

The methods of the invention may be used to screen therapeutic receptor gene promoter transcriptional activators or inhibitors for their effectiveness in altering expression of a gene of interest in vitro or in vivo by the assays described above. Where a non-human mammal is treated or where a therapeutic for a non-human animal is screened, a melatonin 1a receptor gene regulatory region is preferably specific for that species.

Other Embodiments

Melatonin 1a receptor transcriptional regulatory regions according to the invention include any melatonin 1a receptor gene promoters (e.g., regulatory regions as described herein). Such promoters may be derived from any source, but are preferably derived from a vertebrate animal, e.g., a mouse, a human, a sheep, or a frog. These promoters are used, e.g., to screen for transcriptional inhibitors which can be used to alter production of melatonin 1a receptor and thereby alter sensitivity to melatonin in cell lines or in whole transgenic animals.

Specific receptor gene promoter regions of interest include sequences upstream of the transcription start site of the melatonin 1a receptor gene, within the intron, or downstream of the $Mel_{1a}$ coding sequence, which sequences function in a cell to express a gene of interest operably linked to the receptor gene promoter region of the invention. Nucleotide substitutions, deletions, or insertions located at positions of the nucleotide sequence which do not destroy the promoter's ability to initiate transcription or destroy the ability of the resultant mRNA to be translated are within the scope of the present invention.

I claim:

1. A method of screening a candidate compound for the ability to alter transcription from a functional melatonin 1a receptor gene promoter, said method comprising:
   a) providing a cell comprising a recombinant melatonin 1a receptor gene promoter operably linked to a reporter gene;
   b) contacting said cell with said candidate compound; and
   c) detecting expression of said reporter gene in the presence of said candidate compound, wherein an increase or decrease in said expression in the presence of the candidate compound, compared to expression in the absence of the candidate compound, is an indication that the candidate compound alters transcription from the promoter.

2. The method of claim 1, wherein the melatonin 1a receptor gene promoter is the portion of SEQ ID NO:1 comprising transcriptional and translational regulatory sequences.

3. The method of claim 1, wherein the melatonin 1a receptor gene promoter is capable of hybridizing under stringent hybridization conditions to a nucleic acid molecule having a nucleotide sequence complementary to SEQ ID NO:1.

4. The method of claim 1, wherein the melatonin 1a receptor gene promoter has approximately 95% homology to the transcriptional and translational regulatory region of SEQ ID NO:1.

5. The method of claim 1, wherein the melatonin 1a receptor gene promoter comprises bases −1142 to +26 of FIG. 2 (SEQ ID NO:1).

6. The method of claim 5, wherein the nucleotide sequence further comprises bases +1165 to +1606 of FIG. 2 (SEQ ID NO:1).

* * * * *

UNITED STATES PATENT AND TRADEMARK OFFICE
CERTIFICATE OF CORRECTION

PATENT NO.   : 6,037,131
DATED        : March 14, 2000
INVENTOR(S)  : Steven M. Reppert It is certified that error appears in the above-identified patent and that said Letters Patent is hereby corrected as shown below:

<u>Title page,</u>
Item [54], delete "an", insert -- and --
Item [62], Related U.S. Application Data, after 5,889,177 insert -- claims priority from provisional application no. 60/022,185 filed July 18, 1996 --
Item [56], References Cited, OTHER PUBLICATIONS,
Albarracin, et al., delete "Charact4erization", insert -- Characterization --
Chomczynski et al., delete "Gaundinium", insert -- Guandinium --

<u>Column 1,</u>
Line 2, delete "AN", insert -- AND --

<u>Column 4,</u>
Line 62, delete "animals", insert -- animal's --

<u>Column 5,</u>
Line 53, delete "digrams", insert -- diagrams --
Line 53, delete "is a diagram"

<u>Column 7,</u>
Line 28, delete "Receytor", insert -- Receptor --

<u>Column 8,</u>
Line 60, delete "CRNA", insert -- cRNA --
Line 60, delete "$^{32}$p-UTP", insert -- $^{32}$P-UTP --

<u>Column 9,</u>
Line 30, delete "dewit", insert -- de Wet --

<u>Column 11,</u>
Line 4, delete "Receytor", insert -- Receptor --
Line 25, delete "CRNA", insert -- cRNA --
Line 32, delete "MRNA", insert -- mRNA --

UNITED STATES PATENT AND TRADEMARK OFFICE
CERTIFICATE OF CORRECTION

PATENT NO. : 6,037,131
DATED : March 14, 2000
INVENTOR(S) : Steven M. Reppert

It is certified that error appears in the above-identified patent and that said Letters Patent is hereby corrected as shown below:

Column 13,
Line 10, delete "Seguence:", insert -- Sequence: --
Line 67, delete "ordinarily", insert -- Ordinarily --

Column 23,
Line 19, delete "I claim:", insert -- What is claimed is: --

Signed and Sealed this

Thirtieth Day of July, 2002

Attest:

JAMES E. ROGAN
Attesting Officer *Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 2772 base pairs
       (B) TYPE: nucleic acid
       (C) STRANDEDNESS: single
       (D) TOPOLOGY: linear (ix) FEATURE:
       (A) NAME/KEY: Coding Sequence
       (B) LOCATION: 1270...2328
       (D) OTHER INFORMATION: intron coding sequence between
           positions 1464 and 1465

(xi) SEQUENCE DESCRIPTION: SEQ ID NO:1:

```
CGGAGGATGA CCTTGAACCT CTGATCCTTT GCCTTCCCTC CTGGGTGCTG GGGTTACGTG    60

ACTGAGGTGC CACATCCAGT TTATACAGCA CTAGAAATGG AGTCTAAGAT TTTGCAAATG   120

CTGCACAGGA GCCCTAACGA CAGAGCCACA CGCTCAGGCC CCTCAATTCT GCATTGCATT   180

TCTTCTTGAA ATTATTGATG AACACAACCA TTTTACTTAA TATGATTTGT TGAGACAGGA   240

TTTTATACAG CAACACTGAT TGACCACACA GCTCAAGATG CCCCCAAACT GGTGTTGATT   300

CTCCTGCCTC AGCCTCCAGA GCTACGACAC ATTGTTTAAT TTTAATACAG ATTTTAATAT   360

TGTCATGTCA TGCTTTTCTG GTATTCATCT TCTTAAAATG TATTTTCTTC ATTTTTCTTC   420

ACTCTTTCAA AGGGACTTTG GAAATGCTTA GGAATTGGAC AGCCATAAAA TATATGGAGA   480

GCATGAAAAT TTAAGTGTTC AATATGAGAA CATCATATGT TTTGTGTAAG TCTCCTTCCC   540

CATGTTGAAG AAAGTTTTGG GGTTTTGTTC CATTCTGTAC AGAGCTGGCT AATGCACTTC   600

CCAGAAATCT TACACTGTGG TTCTACGTCT GCTTCTATTA TCTCAAGTTT CTGTTTTCAC   660

TGATAGTTTC AAAAGAACAT ATACACCTGT CATCTGCAAA TATTTACATT TTGTTTCGTT   720

TAATTGCCAG AAACACCCAG AACAGACATT AAATCGTGCT ATGCCAGACG GAAAGGGTGT   780

GATTTAATAT CATTATTACT TTATTTTTAC ACATCATTGA CTATTAAAGT TGATGAGTTA   840

GATTCTATTT TCATCTTCAT TTTCCGGATA AGACATCCAG GGCATCTAGT CCTGGTTAGG   900

ATTCAAGTTC GTGAATCGAG GCCTTCCAGG GTGCAAGTTT CCCTCCACTT GATGCCTCCA   960

CGTGTCTCAC CGAGTCTCGC CACACGGGGG CGCAACGTGC ACGCACTGTG GGACCTCCGA  1020

GTCCAAGTTG CTGGGCAGTG GACAGCAGGT GTCAGCAGGC GGCAGTGGCC AAGTGCAGAG  1080

AGGGTGTCCT ACCACCGGGA GGGGGCTGGA GTGGGCAGGA CAGCCGCGAA GCAATCATAA  1140

GGATGCAAAG TAGACGCGGG AGGGCCATAA AAAGTGGCGG AGAGGGCTCG AGCAGAGCTG  1200

AGCAGTTGAG GGCTCCGGGG CGACAGGACA ATGGCCCTGG CTGTGCTGCG GTGAGGCACC  1260

CAGGGGACC  ATG AAG GGC AAT GTC AGC GAG CTG CTC AAT GCC ACT CAG CAG  1311
           Met Lys Gly Asn Val Ser Glu Leu Leu Asn Ala Thr Gln Gln
             1               5                  10

GCT CCA GGC GGC GGG GAG GGA GGG AGA CCA CGA CCG TCC TGG CTG GCC     1359
Ala Pro Gly Gly Gly Glu Gly Gly Arg Pro Arg Pro Ser Trp Leu Ala
 15              20                  25                  30

TCT ACA CTG GCC TTC ATC CTC ATC TTT ACC ATC GTG GTG GAC ATT CTG    1407
Ser Thr Leu Ala Phe Ile Leu Ile Phe Thr Ile Val Val Asp Ile Leu
             35                  40                  45

GGC AAC CTG CTG GTC ATC CTG TCT GTG TAC CGC AAC AAG AAG CTC AGG   1455
```

-continued

| | | | | | | | | | | | | | | | | |
|---|---|---|---|---|---|---|---|---|---|---|---|---|---|---|---|---|
|Gly|Asn|Leu|Leu|Val|Ile|Leu|Ser|Val|Tyr|Arg|Asn|Lys|Lys|Leu|Arg| |
| | | |50| | | | |55| | | | |60| | | |

```
AAC TCA GGG AAT ATA TTT GTG GTG AGT TTA GCT GTG GCA GAC CTC GTG      1503
Asn Ser Gly Asn Ile Phe Val Val Ser Leu Ala Val Ala Asp Leu Val
         65                  70                  75

GTG GCT GTT TAC CCT TAT CCC TTG GTG CTG ACA TCT ATC CTT AAC AAC      1551
Val Ala Val Tyr Pro Tyr Pro Leu Val Leu Thr Ser Ile Leu Asn Asn
 80                  85                  90

GGA TGG AAT CTG GGA TAT CTA CAC TGT CAA GTC AGC GCA TTT CTA ATG      1599
Gly Trp Asn Leu Gly Tyr Leu His Cys Gln Val Ser Ala Phe Leu Met
 95                 100                 105                 110

GGC TTG AGT GTC ATC GGC TCG ATA TTC AAC ATC ACG GGG ATC GCT ATG      1647
Gly Leu Ser Val Ile Gly Ser Ile Phe Asn Ile Thr Gly Ile Ala Met
                115                 120                 125

AAC CGT TAC TGC TAC ATT TGC CAC AGC CTC AAG TAC GAC AAA ATA TAC      1695
Asn Arg Tyr Cys Tyr Ile Cys His Ser Leu Lys Tyr Asp Lys Ile Tyr
                130                 135                 140

AGT AAC AAG AAC TCG CTC TGC TAC GTG TTC CTG ATA TGG ATG CTG ACA      1743
Ser Asn Lys Asn Ser Leu Cys Tyr Val Phe Leu Ile Trp Met Leu Thr
                145                 150                 155

CTC ATC GCC ATC ATG CCC AAC CTG CAA ACC GGA ACA CTC CAG TAC GAT      1791
Leu Ile Ala Ile Met Pro Asn Leu Gln Thr Gly Thr Leu Gln Tyr Asp
160                 165                 170

CCC CGG ATC TAC TCC TGT ACC TTC ACC CAG TCT GTC AGC TCA GCG TAC      1839
Pro Arg Ile Tyr Ser Cys Thr Phe Thr Gln Ser Val Ser Ser Ala Tyr
175                 180                 185                 190

ACG ATA GCA GTG GTG GTT TTC CAT TTC ATC GTG CCT ATG ATT ATT GTC      1887
Thr Ile Ala Val Val Val Phe His Phe Ile Val Pro Met Ile Ile Val
                195                 200                 205

ATC TTC TGC TAC TTA AGG ATA TGG GTC CTG GTC CTT CAG GTC AGA CGG      1935
Ile Phe Cys Tyr Leu Arg Ile Trp Val Leu Val Leu Gln Val Arg Arg
                210                 215                 220

AGG GTG AAA CCC GAC AAC AAG CCC AAA CTG AAG CCC CAG GAC TTC AGG      1983
Arg Val Lys Pro Asp Asn Lys Pro Lys Leu Lys Pro Gln Asp Phe Arg
                225                 230                 235

AAC TTT GTC ACC ATG TTC GTA GTT TTT GTA CTT TTT GCC ATT TGT TGG      2031
Asn Phe Val Thr Met Phe Val Val Phe Val Leu Phe Ala Ile Cys Trp
                240                 245                 250

GCC CCA CTC AAC CTC ATA GGT CTT ATT GTG GCC TCA GAC CCT GCC ACC      2079
Ala Pro Leu Asn Leu Ile Gly Leu Ile Val Ala Ser Asp Pro Ala Thr
255                 260                 265                 270

ATG GTC CCC AGG ATC CCA GAG TGG CTG TTC GTG GCT AGT TAC TAC CTG      2127
Met Val Pro Arg Ile Pro Glu Trp Leu Phe Val Ala Ser Tyr Tyr Leu
                275                 280                 285

GCG TAC TTC AAC AGC TGC CTC AAC GCA ATT ATA TAC GGA CTA CTG AAT      2175
Ala Tyr Phe Asn Ser Cys Leu Asn Ala Ile Ile Tyr Gly Leu Leu Asn
                290                 295                 300

CAG AAT TTC AGA AAG GAA TAC AAA AAG ATT ATT GTC TCG TTG TGC ACA      2223
Gln Asn Phe Arg Lys Glu Tyr Lys Lys Ile Ile Val Ser Leu Cys Thr
                305                 310                 315

GCC AAG ATG TTC TTT GTG GAG AGT TCA AAT GAA GAA GCA GAT AAG ATT      2271
Ala Lys Met Phe Phe Val Glu Ser Ser Asn Glu Glu Ala Asp Lys Ile
320                 325                 330

AAA TGT AAG CCC TCT CCA CTA ATA CCC AAT AAT AAC TTA ATA AAG GTG      2319
Lys Cys Lys Pro Ser Pro Leu Ile Pro Asn Asn Asn Leu Ile Lys Val
335                 340                 345                 350

GAC TCT GTT TAAAAAGCCA GTGGTGCTAG CAGATTATCC ACACTGGTTG GGGTCTTCC   2377
Asp Ser Val

TGCTCTCCTT GTTTGCTTTC TTTTGTCTAG AAATCAGTCT ATCCAACTTG AAGCTCTTCA   2437
```

-continued

```
GGGTTGCCTC CATAGTGTTG GAAAGGATCT CCTGTCTGCC CCATAATCAG ATTGCTAGTA    2497

TCAAGGGGAA TGCTGAACAG GCACACCATA GTTTAAATGG ACAACTTGTA TCAGCAGAGG    2557

AGGTCGTGGT GCAGACTCTC TCGTCTCTGG GGCAACCAGG TCTTGGGGGT TGCCCACATT    2617

TAGGATTACA ATATACAGCA ACAGACCAAA CCTGAACAAA ATGTGGAAGG AACTCAAGAC    2677

AAGAGGGACC ATGGGGACCT TCCTTTTATT GTAAGCGAGT GATACAGAGT GTTTATTCTT    2737

ACCTATGGCT GAATTAAAAT AGTCAAAAAA CTTAA                               2772
```

(2) INFORMATION FOR SEQ ID NO:2:

(i) SEQUENCE CHARACTERISTICS:
        (A) LENGTH: 353 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:2:

```
Met Lys Gly Asn Val Ser Glu Leu Leu Asn Ala Thr Gln Gln Ala Pro
 1               5                  10                  15

Gly Gly Gly Glu Gly Gly Arg Pro Arg Pro Ser Trp Leu Ala Ser Thr
                20                  25                  30

Leu Ala Phe Ile Leu Ile Phe Thr Ile Val Val Asp Ile Leu Gly Asn
            35                  40                  45

Leu Leu Val Ile Leu Ser Val Tyr Arg Asn Lys Lys Leu Arg Asn Ser
        50                  55                  60

Gly Asn Ile Phe Val Val Ser Leu Ala Val Ala Asp Leu Val Val Ala
 65                  70                  75                  80

Val Tyr Pro Tyr Pro Leu Val Leu Thr Ser Ile Leu Asn Asn Gly Trp
                85                  90                  95

Asn Leu Gly Tyr Leu His Cys Gln Val Ser Ala Phe Leu Met Gly Leu
                100                 105                 110

Ser Val Ile Gly Ser Ile Phe Asn Ile Thr Gly Ile Ala Met Asn Arg
            115                 120                 125

Tyr Cys Tyr Ile Cys His Ser Leu Lys Tyr Asp Lys Ile Tyr Ser Asn
        130                 135                 140

Lys Asn Ser Leu Cys Tyr Val Phe Leu Ile Trp Met Leu Thr Leu Ile
145                 150                 155                 160

Ala Ile Met Pro Asn Leu Gln Thr Gly Thr Leu Gln Tyr Asp Pro Arg
                165                 170                 175

Ile Tyr Ser Cys Thr Phe Thr Gln Ser Val Ser Ser Ala Tyr Thr Ile
            180                 185                 190

Ala Val Val Val Phe His Phe Ile Val Pro Met Ile Ile Val Ile Phe
        195                 200                 205

Cys Tyr Leu Arg Ile Trp Val Leu Val Leu Gln Val Arg Arg Arg Val
    210                 215                 220

Lys Pro Asp Asn Lys Pro Lys Leu Lys Pro Gln Asp Phe Arg Asn Phe
225                 230                 235                 240

Val Thr Met Phe Val Val Phe Val Leu Phe Ala Ile Cys Trp Ala Pro
                245                 250                 255

Leu Asn Leu Ile Gly Leu Ile Val Ala Ser Asp Pro Ala Thr Met Val
            260                 265                 270

Pro Arg Ile Pro Glu Trp Leu Phe Val Ala Ser Tyr Tyr Leu Ala Tyr
```

```
            275                 280                 285
Phe Asn Ser Cys Leu Asn Ala Ile Ile Tyr Gly Leu Leu Asn Gln Asn
    290                 295                 300

Phe Arg Lys Glu Tyr Lys Lys Ile Ile Val Ser Leu Cys Thr Ala Lys
305                 310                 315                 320

Met Phe Phe Val Glu Ser Ser Asn Glu Glu Ala Asp Lys Ile Lys Cys
                325                 330                 335

Lys Pro Ser Pro Leu Ile Pro Asn Asn Asn Leu Ile Lys Val Asp Ser
                340                 345                 350

Val
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:3:

GTACACAGAC AGGATGACCA GCAG                      24

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:4:

CAGCAGGTTG CCCAGAATGT CCACCAC                 27

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:5:

TTCAAGCTTA GCCAGGACGG TCGTGGTCTC CCT           33

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:6:

TCAGAATTCG AGTCCAAGTT GCTGGGCAGT GGA           33

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

-continued

```
ACTCAACCTC ATAGGTCTTA TTGT                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

CCAGAGTGGC TGTTCGTGGC TAGT                                              24
```